(12) United States Patent
Savord

(10) Patent No.: US 8,257,260 B2
(45) Date of Patent: Sep. 4, 2012

(54) SYSTEM AND METHOD FOR AMPLIFYING TRANSMIT WAVEFORMS GENERATED BY AN ULTRASONIC SYSTEM

(75) Inventor: Bernard J. Savord, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1433 days.

(21) Appl. No.: 11/571,165

(22) PCT Filed: Jun. 27, 2005

(86) PCT No.: PCT/IB2005/052126
§ 371 (c)(1),
(2), (4) Date: Dec. 22, 2006

(87) PCT Pub. No.: WO2006/003605
PCT Pub. Date: Jan. 12, 2006

(65) Prior Publication Data
US 2008/0097201 A1    Apr. 24, 2008

Related U.S. Application Data

(60) Provisional application No. 60/583,490, filed on Jun. 28, 2004.

(51) Int. Cl.
*A61B 8/00* (2006.01)

(52) U.S. Cl. ....................................................... 600/443

(58) Field of Classification Search .................... 600/443
See application file for complete search history.

(56) References Cited

U.S. PATENT DOCUMENTS

| | | | | |
|---|---|---|---|---|
| 4,222,274 A * | 9/1980 | Johnson | .......................... | 73/607 |
| 4,267,584 A * | 5/1981 | McKeighen et al. | ........... | 367/11 |
| 5,351,692 A * | 10/1994 | Dow et al. | ...................... | 600/463 |
| 5,997,479 A | 12/1999 | Savord et al. | | |
| 6,312,379 B1 * | 11/2001 | Bradley et al. | ................ | 600/437 |
| 6,312,386 B1 * | 11/2001 | Bolorforosh et al. | ......... | 600/447 |
| 6,368,276 B1 * | 4/2002 | Bullis | ............................ | 600/437 |
| 7,181,356 B2 * | 2/2007 | Coperet | ......................... | 702/91 |
| 2001/0043090 A1 * | 11/2001 | Savord | .......................... | 327/108 |
| 2001/0056236 A1 * | 12/2001 | Angelsen | ...................... | 600/458 |
| 2002/0045830 A1 * | 4/2002 | Powers et al. | ................. | 600/459 |
| 2003/0199763 A1 | 10/2003 | Angelsen | | |
| 2004/0030227 A1 | 2/2004 | Littrup et al. | | |

\* cited by examiner

*Primary Examiner* — Brian Casler
*Assistant Examiner* — Saurel J Selkin
(74) *Attorney, Agent, or Firm* — W. Brinton Yorks, Jr.

(57) ABSTRACT

An ultrasonic imaging system has an ultrasonic probe which improves poor harmonic performance of existing transmit circuits through the use of a linear high-voltage transmit amplifier on each sub-channel to amplify low-voltage arbitrary shape transmit waveforms generated by the ultrasonic system. The linear high-voltage amplifier of the ultrasonic probe amplifies low-voltage arbitrary shape transmit waveforms beamformed by a micro-beamformer of the ultrasonic system.

9 Claims, 2 Drawing Sheets

Figure 1:
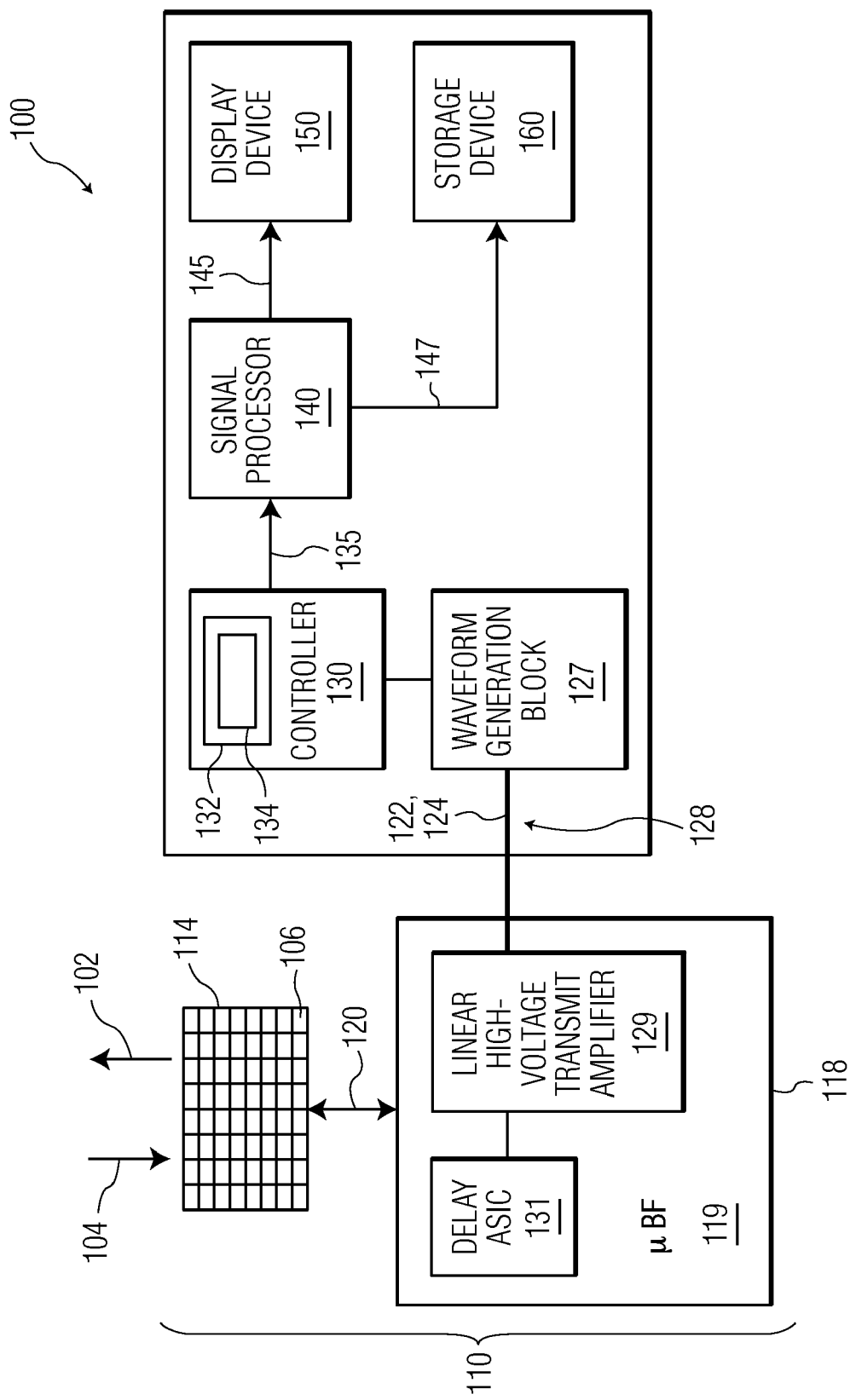

SYSTEM AND METHOD FOR AMPLIFYING TRANSMIT WAVEFORMS GENERATED BY AN ULTRASONIC SYSTEM

The present invention relates generally to ultrasonic imaging systems. More particularly, it relates to a system and method for amplifying low-voltage arbitrary shape transmit waveforms beam-formed by a micro-beam-former of a ultrasonic imaging system to improve harmonic imaging.

Ultrasonic transducers are used in many medical applications and, in particular, for the non-invasive acquisition of images of organs and conditions within a patient, typical examples being the ultrasonic imaging of fetuses and the heart. The ultrasonic transducers used in such applications are generally hand held, and must meet stringent dimensional constraints in order to acquire the desired images. It is frequently necessary that the transducer be able to obtain high resolution images of particular portions of a patient's body when using endoscopic ultrasonic imaging equipment.

Typically, conventional ultrasonic imaging equipment use one-dimensional and two-dimensional arrays for acquiring the ultrasonic images of particular tissues or organs within the patient's body. Generally, these arrays include a plurality of acoustic elements arranged in a planar configuration. Beam steering and beam tractor-treading are used in such systems to control the propagation of the output ultrasonic beam such that the output beam may be steered along a horizontal axis and/or along a vertical axis. Employing these methods allows ultrasonic systems to receive transmit waveforms which are processed using harmonic imaging to acquire images of the particular region of the patient's body.

Existing matrix probe waveforms are generally limited to simple square "bang-bang" transmit waveforms. Such waveforms, however, have poor performance when used for harmonic imaging due to their strong transmitted harmonic energy. Therefore, a need exists for an improved ultrasonic imaging system capable of improving poor harmonic performance.

It is an object of the present invention to provide an ultrasonic system having an ultrasonic probe which improves poor harmonic performance of existing transmit circuits through the use of a linear high-voltage transmit amplifier on each sub-channel.

An ultrasonic imaging system having an ultrasonic probe which improves poor harmonic performance of existing transmit circuits through the use of a linear high-voltage transmit amplifier on each sub-channel to amplify low-voltage arbitrary shape transmit waveforms generated by the ultrasonic system is hereinafter disclosed. In particular, the linear high-voltage amplifier of the ultrasonic probe amplifies low-voltage arbitrary shape transmit waveforms beam-formed by a micro-beam-former of the ultrasonic system.

Specifically, system transmit waveforms are either transmitted at a low-voltage or voltage divided down in order to be handled by a low-voltage analog delay ASIC. This signal is delayed a programmable amount in order to provide transmit beam formation, and then sent to the linear high-voltage transmit amplifier. The analog delay can be the same one that is used to beam-form receive signals. To share between transmit and receive, one can use analog T/R switches to control the direction of signals through the delay line.

Figure 2:
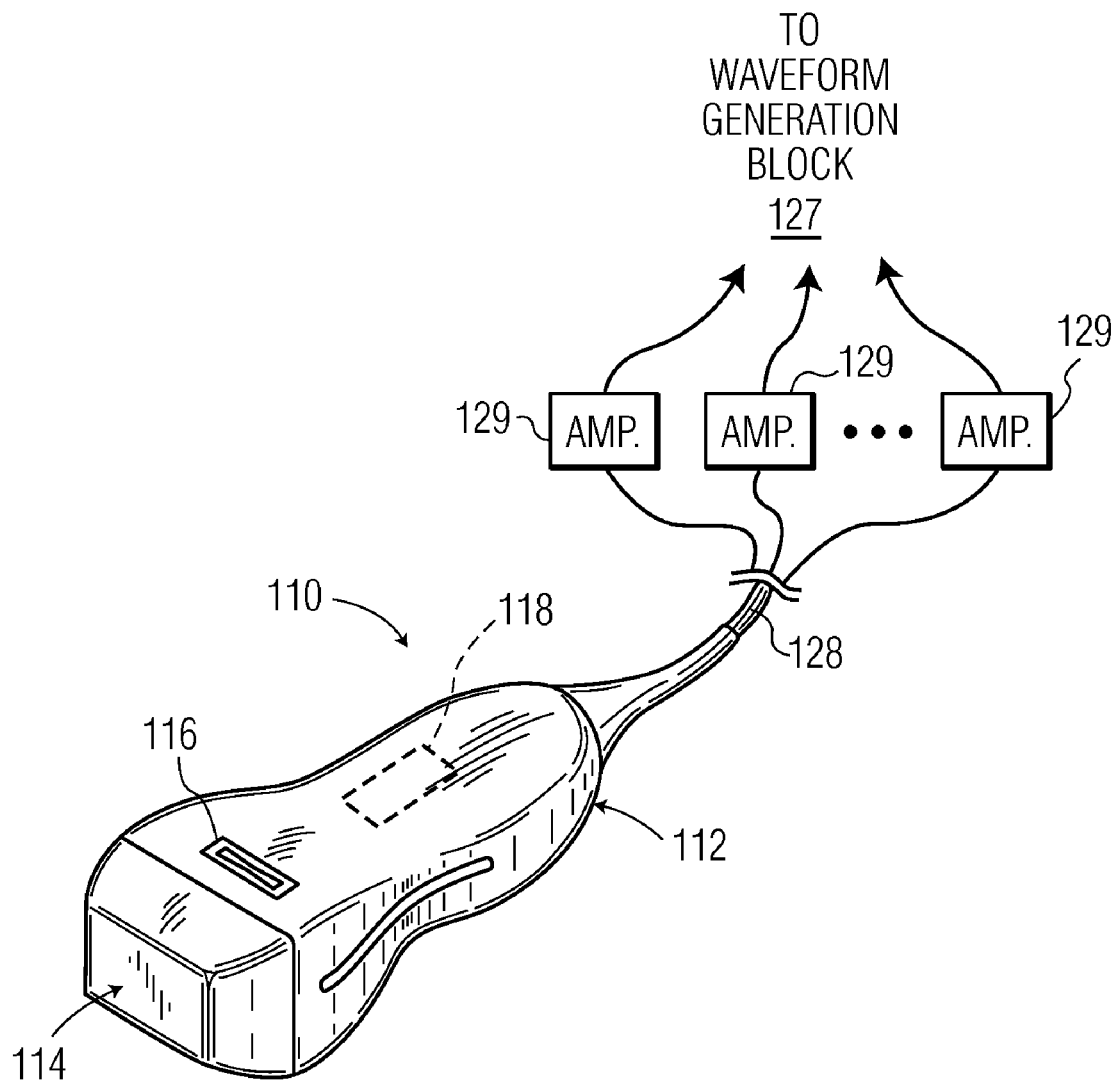

The foregoing objects and advantages of the present invention may be more readily understood by one skilled in the art with reference being had to the following detailed description of preferred embodiments thereof, taken in conjunction with the accompanying drawings in which:

FIG. 1 is a block diagram of an ultrasonic imaging system having a linear high-voltage amplifier for amplifying low-voltage arbitrary shape transmit waveforms beam-formed by a micro-beam-former of the ultrasonic imaging system in accordance with the present invention; and FIG. 2 is a perspective view of the ultrasonic probe and several linear high-voltage amplifiers of the ultrasonic imaging system shown by FIG. 1.

An ultrasonic imaging system according to the present invention is shown by FIG. 1, and further described with specificity hereinafter. The ultrasonic imaging system 100 includes an ultrasonic probe 110 having a housing 112, an ultrasonic transducer assembly 114, a selector switch 116 (FIG. 2), and associated circuitry 118 which includes a micro-beam-former 119. The ultrasonic probe 110 is preferably a Matrix TEE probe.

The ultrasonic transducer assembly 114 includes a plurality of acoustic elements arranged in a number of columns and rows for generating at least one acoustic beam 102 and/or receiving at least one echo signal 104. The ultrasonic transducer assembly 114 is configured and adapted to fit within the housing 112. The acoustic elements are preferably configured and arranged in a generally planar configuration, although other configurations and arrangements, such as convex or cylindrical two-dimensional arrays are contemplated.

Each acoustic element is formed from a suitable piezoelectric material and is capable of generating an acoustic pulse at a particular frequency when a driver signal is applied to the acoustic element. A number of acoustic pulses are combined into the acoustic beam 102 for impinging an acoustic target, where at least some of the energy in the acoustic beam 102 is reflected back towards the transducer assembly 114 as echo signal 104. In addition, each acoustic element is capable of receiving the echo signal 104 from the acoustic target and generating a corresponding output signal 120. The ultrasonic imaging system has a controller 130 for generating a drive signal 122 and for electronically steering the acoustic beam 102.

Two-dimensional transducer arrays are generally employed with accompanying circuitry to produce three-dimensional ultrasonic images of the acoustic target since the acoustic beam 102 is generated by acoustic elements in both the rows and the columns of the two-dimensional transducer array. By controlling the phase differential, or the time delay, among the acoustic elements that are driven by the controller 130, a number of acoustic pulses are combined into the acoustic beam 102 that can be electronically steered by the controller 130 to acquire acoustic targets within the field of view of the ultrasonic probe 110. It is contemplated that a number of the acoustic elements in the transducer assembly 114 may be "passive" elements (i.e. not configured for generating acoustic pulses or receiving echo signals) while the remaining acoustic elements are "active" elements (i.e. configured for generating an acoustic pulse and receiving an echo signal 104). In addition, the ultrasonic imaging system 100 further includes a signal processor 140, a display device 150, and a storage device 160.

Still referring to FIG. 1, the controller 130 is coupled to the ultrasonic probe 110 via a waveform generation block 127 and a connecting means 128 for communicating the drive signal 122 to one or more of the acoustic elements of the transducer assembly 114. Additionally, the connecting means 128 communicates a control signal 124 and the output signal 120 between the ultrasonic probe 110 and the waveform generation block 127. More specifically, the controller 130 is operatively coupled to the ultrasonic transducer assembly 114 via the waveform generation block 127 for varying characteristics and properties of the generated acoustic beam 102 as discussed in further detail hereinafter. The waveform generation block 127 sends waveforms to the ultrasonic probe 110.

The connecting means 128 includes a linear high-voltage transmit amplifier 129 on each sub-channel (as shown by FIG. 2) to amplify low-voltage arbitrary shape transmit waveforms generated by the ultrasonic probe 110, thereby improving poor harmonic performance of existing transmit circuits. The amplifier operates in the range of 20 to 200 volts and preferably, in the range of 10 to 100 volts for amplifying waveforms generated in the 0 to 5 volt range to 0-100 volts. In particular, the linear high-voltage amplifier 129 amplifies low-voltage arbitrary shape transmit waveforms beamformed by the micro-beam-former 118 of the ultrasonic imaging system 100.

Specifically, system transmit waveforms (signal 120) are either transmitted at a low-voltage or voltage divided down by a voltage divider (not shown) in order to be handled by a low-voltage analog delay ASIC 131. The signal 120 is delayed a programmable amount by the delay ASIC 131 in order to provide transmit beam formation, and then sent to the linear high-voltage transmit amplifier 129. The analog delay can be the same one that is used to beam-form receive signals (e.g., drive signals 122). Preferably, the delay time is 0 to 1 usec. To share between transmit and receive, one can use analog T/R switches to control the direction of the signals through the delay line of connecting means 128. It is contemplated that one or more of the amplifiers 129 for each subchannel can be housed within the ultrasonic probe 110, the controller 130 and/or other component of the ultrasonic imaging system 100.

The controller 130 generates a plurality of driver signals 122 that correspond to the number of acoustic elements to be activated. The controller 130 further controls the timing of the respective driver signals 122 applied to the acoustic elements (i.e. phase shifting). In a preferred embodiment, the controller 130 includes a user interface 132 and associated circuitry for controlling the timing of the drive signals 122. It is further contemplated that more than one acoustic element in the ultrasonic transducer assembly 114 may be activated by the controller 130 simultaneously thereby forming an active aperture producing the acoustic beam 102. Advantageously, the user interface 132 is operable by an operator to adjust and/or control the active aperture for acquiring the desired image. In addition, the user interface 132 is configured and adapted for affecting other aspects of the ultrasonic imaging system 100, such as starting and stopping the system, directing the image information to the display device 150, directing the image information to the storage device 160, and retrieving the image information from the storage device 160.

The controller 130 is operatively coupled to the ultrasonic transducer assembly 114 for varying characteristics and properties of the generated acoustic pulses that are included in the acoustic beam 102. The controller 130 generates a plurality of drive signals 122 that correspond to the number of acoustic elements to be activated. The controller 130 further controls the timing of the respective drive signals 122 applied to the acoustic elements (i.e. phase shifting), and the resulting acoustic beam 102 is initially generated at a first end of the ultrasonic transducer assembly 114 and advances towards a second end.

More specifically, when the acoustic beam 102 is initially formed, a number of the active acoustic elements disposed in the ultrasonic transducer assembly 114 is actuated simultaneously by corresponding drive signals 122 from the controller 130. In one embodiment, the acoustic elements are arranged in a number of rows and columns to form an array where the controller 130 activates a predetermined number of acoustic elements in the rows and columns to form the acoustic beam 102.

Alternatively, the controller 130 can actuate a number of active acoustic elements in a number of columns where the number of acoustic elements activated is less than the number of active acoustic elements in each of the columns thereby forming a smaller active aperture and acoustic beam 102. Preferably, the controller 130 causes the generation of acoustic beam 102 within the active aperture and the controller 130 is adapted to move the active aperture and the acoustic beam 102 along the row of acoustic elements. After the active aperture reaches the end of the row of acoustic elements, the controller 130 shifts the acoustic beam 102 and the active aperture by the number of previously activated columns and causes the active aperture to advance. By advantageously controlling the motion and direction of the acoustic beam 102 and resultant active aperture, a three-dimensional volume is obtainable.

In one embodiment, the associated circuitry in the controller 130 generates the control signal 124 in response to selections made by the operator in the user interface 132. The user interface 132 includes one or more user operable controls such as a rocker switch, a button, a trackball, a touchpad, a pointing stick, etc. These user operable controls permit the user to control various features and aspects of the ultrasonic imaging system 100, such as field of view of the ultrasonic probe 110, local control of the ultrasonic probe 110 (i.e. controlled by the user interface 132), or remote control of the ultrasonic probe 110 (i.e. controlled by the selector switch 116). In turn, the control signal 124, in cooperation with the associated circuitry, generates the number of drive signals 122 to generate the acoustic beam 102. In addition, the control signal 124 cooperates with the associated circuitry to control the timing of the drive signals 122, thereby controlling the active aperture and the acquired image.

In a preferred embodiment, the control signal 124 is generated by the associated circuitry 118 of the ultrasonic probe 110. More particularly, the selector switch 116 cooperates with the associated circuitry 118 to generate the control signal 124. In turn, the control signal 124 is communicated to the associated circuitry of the controller 130 via the connecting means 128. The generation and control of the drive signals 122 by the control signal 124 are identical to the previous embodiment, where the control signal 124 was generated in the controller 130. As shown by FIG. 2, the selector switch 116 is user operable for controlling characteristics of the acquired image by controlling the generation and timing of the drive signals 122. The selector switch 116 may be a rocker switch, a button, a trackball, a touchpad, a pointing stick, etc.

More particularly, when the user selects local control of the ultrasonic probe 110, the associated circuitry in the controller 130 generates the control signal 124 according to user selections on the user interface 132. Preferably, the user interface 132 includes a control device 134 having at least two positions or states for controlling the associated circuitry in response to the user's selections. The control device 134 may be a rocker switch, a button, a trackball, a touchpad, a pointing stick, etc. The control signal 124 has unique characteristics for each position or state of the control device 134. Therefore, by selecting a position on the control device 134, the user controls the associated circuitry for controlling the control signal 124 and the acquired image. For example, the operator can steer the planes of the scan in preselected modes such as lateral tilt, elevational tilt, or rotation.

By advantageously providing the selector switch 116 and the associated circuitry 118 on the ultrasonic probe 110, the operator can readily control some of the operations of the ultrasonic imaging system 100 from the ultrasonic probe 110 and need not operate user interface 132 located on the system unit. When controlling the ultrasonic probe 110 remotely, the selector switch 116 in cooperation with the associated circuitry in the ultrasonic probe 110 generates the control signal 124. Similar to local control of the ultrasonic probe 110, the associated circuitry generates the control signal 124 having unique characteristics for each position or state of the selector switch 116. Therefore, by selecting a position on the selector switch 116, the user controls the associated circuitry for controlling the control signal 124 and the acquired image. For example, the operator can steer the planes of the scan in preselected modes such as lateral tilt, elevational tilt, or rotation. Additionally, by controlling the control signal 124, and therefore the drive signals 122, from the ultrasonic probe 110 reduces the need for binding the user interface 132 to the modes of operation of the ultrasonic imaging system 100.

For example, the operator positions the ultrasonic probe 110 in contact between a patient's ribs, then holds the ultrasonic probe 110 stationary while electronically steering the scan using the same hand to operate the selector switch 116. In one embodiment, the selector switch 116 and the associated circuitry 118 adjust the binding based on the mode of operation of the ultrasonic imaging system 100. For example, when using Flow mode or Doppler mode, the generated control signal 124 moves the region of interest, whereas in the Live 3D mode, it rotates the displayed volume. Alternatively, the binding of the selector switch 116 may be user selectable.

The connecting means 128 is generally a cable including a plurality of conducting elements, such as wires. Alternatively, the connecting means 128 can significantly be improved if some of the electronics are located in the ultrasonic probe housing 112 and the connecting means is a wireless connection, such as infrared or radio frequency.

This output signal 120 is communicated through the controller 130 to the signal processor 140. In the signal processor 140, the output signal 120 of the transducer assembly 114 is transformed by associated circuitry in the signal processor 140 to generate an image signal 145. A display device 150 is operatively coupled to an output of the signal processor 140 for receiving one or more image signals 145 and for transforming the image signals 145 into a video image. Essentially, the display device 150 is capable of displaying data corresponding to the at least one image signal 145. It is preferred that the display device 150 be a video monitor that is readily viewable by attending personnel.

Alternatively, the associated circuitry in the signal processor 140 produces a data signal 147 in addition to, or in lieu of the image signal 145. In an embodiment where signal processor produces the data signal 147 in addition to the image signal 145, it is preferred that the data signal 147 includes substantially identical information as contained in the image signal 145. A storage device 160 is operatively coupled to an output of the signal processor 140 for receiving one or more data signals 147 and for transforming the at least one data signal 147 into an organized sequence representing the information included in the at least one data signal 147. Essentially, the storage device 160 is capable of storing data corresponding to the at least one data signal 147. It is preferred that the storage device is a magnetic storage device such as a magnetic disc or a magnetic tape. More preferably, the storage device is a hard drive. It is contemplated that other storage devices such as optical storage devices may be used in lieu of the hard drive without departing from the scope or spirit of the present invention.

In another embodiment, the user interface 132 is further adapted and configured to cooperate with the associated circuitry in the signal processor 140 for retrieving the data stored in the storage device 160. In this embodiment, the storage device 160 transforms the stored data into at least one data signal 147 that is communicated to the associated circuitry of the signal processor 140. The associated circuitry of the signal processor 140 transforms the at least one data signal 147 into at least one image signal 145. The at least one image signal 145 is then communicated to the display device 150 for viewing as previously discussed.

The described embodiments of the present invention are intended to be illustrative rather than restrictive, and are not intended to represent every embodiment of the present invention. Various modifications and variations can be made without departing from the spirit or scope of the invention as set forth in the following claims both literally and in equivalents recognized in law.

The invention claimed is:

1. An ultrasonic imaging apparatus comprising:
an ultrasonic probe having a housing;
a two-dimensional ultrasonic transducer array assembly configured to fit within the housing, the ultrasonic transducer array including acoustic elements connected to sub-channels of a micro-beam-former for generating at least one acoustic beam and/or receiving at least one echo signal;
the micro-beam-former being located within said housing and operatively coupled to said ultrasonic transducer assembly for controlling the at least one acoustic beam; and
the micro beamformer having a linear high-voltage transmit amplifier on each of the sub-channels for amplifying low-voltage arbitrary shape transmit waveforms extending over a low voltage range and producing high voltage arbitrary shape waveform transmit signals extending over a high voltage range and transmitted by the two-dimensional ultrasonic transducer array assembly.

2. The ultrasonic imaging apparatus of claim 1, wherein said transmit amplifier operates at a voltage range of 20 to 200 volts.

3. The ultrasonic imaging apparatus of claim 1, wherein said transmit amplifier operates at a voltage range of 10 to 100 volts.

4. The ultrasonic imaging apparatus of claim 1, wherein the signals amplified by the transmit amplifier are low-voltage arbitrary shape transmit waveforms beam-formed by the micro-beam-former.

5. The ultrasonic imaging apparatus of claim 1, wherein the micro-beam-former further comprises a delay circuit for delaying the signals transmitted by the two-dimensional ultrasonic transducer array assembly by a programmable amount.

6. The ultrasonic imaging apparatus of claim 5, wherein the programmable amount is in a range of 0 to 1 μsec.

7. The ultrasonic imaging apparatus of claim 1, wherein the micro-beam-former further comprises a signal processor coupled to said two-dimensional ultrasonic transducer array assembly for processing the at least one echo signal, thereby forming at least one image signal;
a connecting device configured to connect said ultrasonic probe to an ultrasonic imaging apparatus; and
a display for displaying the at least one image signal.

8. The ultrasonic imaging apparatus of claim 1, wherein a controller is operatively coupled to said ultrasonic transducer array assembly, said controller producing a drive signal for operating the ultrasonic transducer array assembly to generate the at least one acoustic beam.

9. The ultrasonic imaging apparatus of claim 1, wherein the probe further comprises a switch configured to provide control of the ultrasonic imaging apparatus using a same hand of an operator for holding the ultrasonic probe stationary while electronically steering the at least one acoustic beam using the same hand to operate the switch.

* * * * *